(12) United States Patent
Haynes et al.

(10) Patent No.: US 6,309,661 B1
(45) Date of Patent: *Oct. 30, 2001

(54) SOLID POLYSACCHARIDE MATERIALS FOR USE AS WOUND DRESSINGS

(76) Inventors: Carla A. Haynes, 35 Brownside Road, Cambuslang, Glasgow G72 8NH; Elaine Lorimer, 68 Grangeneuk Gardens, Balloch, Cumberhauld G68 9BP, both of (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/032,607

(22) Filed: Feb. 27, 1998

(30) Foreign Application Priority Data

Feb. 28, 1996 (GB) .................................... 9604182
Feb. 27, 1997 (EP) .................................... 97301332

(51) Int. Cl.⁷ ........................................ A61F 2/00
(52) U.S. Cl. ................. 424/426; 424/444; 514/953
(58) Field of Search ...................... 424/444, 428; 514/953

(56) References Cited

U.S. PATENT DOCUMENTS

| | | |
|---|---|---|
| D. 370,263 | 5/1996 | Falkenberg et al. . |
| 3,902,559 | 9/1975 | Everingham et al. . |
| 4,341,207 * | 7/1982 | Steer et al. ............ 128/155 |
| 4,394,930 | 7/1983 | Korpman . |
| 4,415,388 | 11/1983 | Korpman . |
| 4,524,064 | 6/1985 | Nambu . |
| 4,624,868 | 11/1986 | Muller . |
| 4,675,009 | 6/1987 | Hymes et al. . |
| 4,692,273 | 9/1987 | Lawrence . |
| 4,994,277 * | 2/1991 | Higham et al. ............ 424/443 |
| 5,009,890 | 4/1991 | DiPippo . |
| 5,059,189 | 10/1991 | Cilento et al. . |
| 5,424,064 | 6/1995 | Schmidt et al. . |
| 5,456,745 | 10/1995 | Roreger et al. . |
| 5,620,706 | 4/1997 | Dumitriu et al. . |
| 5,804,213 * | 9/1998 | Rolf ............................ 424/445 |

FOREIGN PATENT DOCUMENTS

| | | |
|---|---|---|
| 43 43 947 A1 | 6/1995 | (DE) . |
| 0 030 435 | 6/1981 | (EP) . |
| 0 049 944 | 4/1982 | (EP) . |
| 0 227 553 | 7/1987 | (EP) . |
| 0 307 187 | 3/1989 | (EP) . |
| 0 340 945 | 11/1989 | (EP) . |
| 0 454 358 A2 | 10/1991 | (EP) . |
| 1 534 626 | 12/1978 | (GB) . |
| 1 554 002 | 10/1979 | (GB) . |
| 90/14110 | 11/1990 | (WO) . |
| 91/06323 | 5/1991 | (WO) . |
| 93/06802 | 4/1993 | (WO) . |
| 94/02029 | 2/1994 | (WO) . |
| 94/17137 | 8/1994 | (WO) . |
| 95/17147 | 6/1995 | (WO) . |

OTHER PUBLICATIONS

Derwent Abstract Accession No. 91–298476/41, class D17, JP03–196834 A2 by Asahi Optical KK, 1991.
Search Report for EP 97 30 1332 (corresponding EPO application).
Search Report for 9604182.7 (corresponding Great Britain application).

* cited by examiner

Primary Examiner—Diana Dudash
Assistant Examiner—Alysia Berman
(74) Attorney, Agent, or Firm—James Harrington

(57) ABSTRACT

Solid, bioabsorbable materials for use as wound dressings comprise at least 50% by weight of a mixture of xanthan and at least one galactomannan, such as guar gum or locust bean gum. The weight ratio of xanthan: total galactomannans is in the range 1:99 to 99:1, preferably 10:99 to 99:10. The material is preferably made in the form of a sponge by freeze drying a mixed aqueous gel of the xanthan and galactomannans.

10 Claims, No Drawings

SOLID POLYSACCHARIDE MATERIALS FOR USE AS WOUND DRESSINGS

The present invention relates to solid polysaccharide materials that are particularly suitable for use as wound dressings.

It is known to use biopolymers in both naturally occurring and chemically modified forms as wound dressings, either alone or in combination with other materials. Various biopolymers and derivatives have been found to accelerate wound healing, reduce infection and/or reduce scarring when used as wound dressings. The advantages of biopolymers can include low cost and low antigenicity. In addition, the water absorbency, gelling and humectant properties of biopolymers can help to maintain the desired fluid balance at the surface of the wound. In addition, many biopolymers are naturally bioabsorbable, which eliminates the trauma normally associated with removal of a non-bioabsorbable dressing from the surface of a wound. Finally, certain biopolymers such as collagen have been found to exhibit a positive therapeutic effect on wound healing by promoting the growth of certain wound healing cells. All of these advantages have resulted in much research activity in the field of biopolymer wound dressings, and a large number of patent applications.

The two main classes of biopolymers are polypeptides and polysaccharides. Of the polysaccharides, most interest has focused on wound dressings and wound treatment compositions containing alginic acid and the salts and derivatives thereof. Alginate gels, films, fibres and/or fabrics have been proposed as wound dressings. The solubility of the alginate is regulated by varying the ratio of sodium alginate (soluble) to calcium alginate (insoluble) in the compositions.

EP-A-0227553 describes a freeze-dried sodium/calcium alginate sponge for use as a wound dressing. The sponge is formed by mixing an aqueous solution of sodium alginate with a solution of calcium chloride in an inert atmosphere, followed by freeze-drying the mixture. We have found that alginate sponges formed in this way are either too soluble (at high sodium contents), or too brittle (at high calcium contents) to be optimal for use as wound dressings.

Many other polysaccharides have been proposed for use as or in wound dressing materials. These polysaccharides include glucosaminoglycans, such as hyaluronic acid and its derivatives and heparan, and other naturally occurring polysaccharides, especially chitin. It has also been suggested to use naturally occurring polysaccharide gums to form wound dressing gels. In particular, WO-A-9106323 and WO-A-9306802 teach the use of xanthan or guar gums as gelling agents in the preparation of wound dressing gels. However, these references do not appear to teach the use of freeze-dried sponges as wound dressings, and also do not appear to teach the use of gels containing both xanthan and a galactomannan gum, such as guar gum.

U.S. Pat. No. 4994277 describes aqueous gels containing xanthan for use in surgery to reduce tissue adhesions. The gels may also contain a galactomannan such as guar gum to increase viscosity or gelation.

U.S. Pat. No. 4341207 describes a multi-layer decubitus ulcer dressing including a wound contacting layer comprising a mixture of one or more water soluble or swellable hydrocolloids such as guar gum and a natural or synthetic viscous substance, such as a rubber, which acts as a binder for the hydroclloids.

It is an object of the present invention to provide improved solid bioabsorbable materials for use as wound dressings. The desired properties for the improved materials include high liquid absorbency, durable but controllable consistency, low solubility in body fluids, bioabsorbability and low cost. The materials of the present invention further provide related advantages.

It is a further object of the present invention to provide a method of making solid bioabsorbable materials having the above desired characteristics.

Accordingly, the present invention provides a solid bioabsorbable material for use as a wound dressing, said material comprising at least 50% by weight of a mixture of xanthan and at least one galactomannan such that the weight ratio of xanthan: total galactomannans is 1:99 to 99:1.

It has been found that, whilst solid materials formed from xanthan alone or galactomannan alone are soluble in water, and hence unacceptable for most wound dressing applications, the use of a mixture of these two polysaccharide types results in a material having a lower, highly controllable solubility that can be optimised for each wound dressing application. Preferably, the weight ratio of xanthan to total galactomannans is in the range 10:90 to 90:10. More preferably, the ratio is in the range 25:75 to 75:25.

Galactomannans are polysaccharides containing both galactose and mannose residues. Preferably, the galactomannans are selected from the group consisting of guar gums (wherein the galactose to mannose ratio is about 1:2), locust bean gums (wherein the galactose to mannose ratio is about 1:4) and mixtures thereof. Preferably, at least 75% by weight of the solid bioabsorbable material consists of the mixture of xanthan and galactomannans. More preferably, at least 90% by weight of the material consists of the said mixture. The balance of the material comprises water (up to about 10% by weight), optionally salts such as sodium chloride, and therapeutic agents including antiseptics such as silver sulfadiazine or chlorhexidine, antibiotics such as penicillin tetracyclin or streptomycin, steroids and the like. Particularly preferred therapeutic agents in the wound dressing materials are those that actively promote wound healing such as glycosaminglycans (e.g. hyaluronic acid, heparan sulfate or chondroitin sulfate) and in particular cell growth factors, such as fibroblast growth factor and platelet derived growth factor. The therapeutic agents are preferably present in an amount up to 10% by weight, more preferably 0.01–2% by weight of the material.

The materials according to the present invention may be in any solid form, such as solid films or pellets. However, preferably, the materials are in the form of a sponge.

The sponge material according to the present invention may be provided in any shape, but is preferably provided as a wound dressing layer having a thickness of from 1 to 5 mm. Preferably, the sponge material has a water absorbency as hereinafter defined of at least 25 g/g.

The present invention also provides a method of making a solid bioabsorbable material for use as a wound dressing, the method comprising: dispersing a mixture of xanthan and one or more galactomannans in the weight ratio xanthan: total galactomannans range from 1:99 to 99:1 in a solvent to form a mixed dispersion, and freeze-drying the dispersion to produce the material in the form of a sponge.

Preferably, the dispersion in a solution or gel, and the solvent is an aqueous solvent, more preferably the solvent consists essentially of water. Preferably, the total weight concentration of the xanthan and the galactomannans in the dispersion is in the range of 2 to 20 mg/ml. The dispersion will typically be a transparent aqueous gel.

Specific embodiments of the present invention will now be described further, by way of example, as follows.

EXAMPLE 1

Preparation of Sponges

Freeze-dried xanthan/galactomannan sponges as set forth Table I are prepared as follows:

The materials for the sponges are: xanthan gum (Sigma, G1253, practical grade, Merck index (11th edition) #9966, page 9965); guar gum (Sigma, G4129, lab grade, Merck index (11th edition) #4486, page 20); locust bean gum (Sigma, B0753, lab grade, Merck index #5436, page 873).

A 0.5% w/v solution of xanthan gum are prepared by dissolving 5 g of the xanthan gum in 1 litre of water heated to 80° C., followed by cooling to ambient temperature.

Solutions at 0.5% w/v of guar and locust bean gum are prepared by, first, dissolving 20 g of the gum in 1 liter of water heated to 80° C., followed by cooling. The solution is centrifuged at 10,000 rpm for 20 minutes to remove seed pods. The solids content of the solution is then determined by weighing the solution before and after drying in an oven at 105° C. to constant weight, and the solution is then diluted to 0.5% w/v solids content.

The sponges are prepared by mixing the 0.5% w/v xanthan gum solution with the 0.5% w/v guar gum and/or locust bean gum solutions in the ratios specified in Table I, followed by homogenising and degassing the resulting mixture. The mixture is then poured to a depth of 5–10 mm in petri dishes, frozen at −30° C. for at least 20 minutes, and then freeze-dried dried (normal cycle −30 to +25° C. overnight) to produce the sponge.

The advantageous properties of the sponges according to the present invention are determined by means of the following procedures.

Procedure 1 Absorbency Measurements

Examples of the sponge materials in the shape of layers 1–5 mm thick and 1–4 cm$^2$ are conditioned overnight in a relative humidity chamber at about 66% relative humidity at ambient temperature. An absorbency buffer solution (0.01M phosphate buffered saline at pH 7.2) is equilibrated at 37° C. Approximately 20 ml aliquots of the buffer are placed in containers. The sponge samples are weighed, and then added to the aliquots of buffer and incubated for 30 minutes at 37° C. to complete swelling of the samples. The fully swelled samples are then weighed, and the absorbency is calculated in g/g (grams of buffer absorbed per gram of sponge).

This method is similar to that of the surgical Materials Testing Laboratory (SMTL) method for measuring absorption capacity of alginate sheet dressings (TM-46 provision 0.17$), except that the SMTL uses a calcium/sodium buffer. The comparative figures for alginate dressings documented for SMTL absorbency determination are 19.9±2.0 g/g for Kaltostat (Registered Trade Mark), and 15.1±2.0 g/g for Sorbsan (Registered Trade Mark), and 12.8±0.9 g/g for Algosteril (Registered Trade Mark).

Procedure 2 Disintegration Test

The length of time taken for composite sponges of xanthan/galactomannan to disintegrate in a cell culture medium incubated at 37° C. is determined as follows.

Two squares (1.5 by 1.5 cm) of each sponge sample are added to 15 ml of culture medium (Dulbecco's modification of Eagles medium supplemented with 10% fetal calf serum) in a 30 ml Sterilin (Registered Trade Mark) container. Initial observations are made, and then the samples are incubated in a water bath at 37° C. on the minimum shaking speed. Further observations are made at 17, 53, 65, 89 and 163 hours (or approximately 1, 2, 3, 4 and 7 days).

Comparative tests are carried out on pure xanthan sponges, pure galactomannan sponges, Kaltostat (Registered Trade Mark of Britcair) rope (a calcium sodium alginate material with a 2:1 ratio Guluronic acid to mannuronic acid); Algosteril (Registered Trade Mark of Johnson & Johnson) calcium alginate fibrous pad; and Sorbsan (Registered Trade Mark of Steriseal) Fibrous calcium alginate pad.

The results are set forth in Table II. It can be seen that composite sponges of xanthan with galactomannan remained intact in the culture medium longer than sponges of the individual gums. This suggests that there is a synergy between the two components that results in a more robust sponge structure. The resistance to disintegration of the xanthan/galactomannan sponges is comparable to that of commercially available fibrous pads of calcium alginate.

The above specific embodiments have been described for the purposes of illustration only. Many other embodiments falling within the scope of the accompanying claims will be apparent to the skilled reader.

TABLE I

| Gums | Ratio | % Solids | Absorbency g/g | Appearance |
|---|---|---|---|---|
| X/LBG | 70:30 | 0.7 | 31.2 ± 18.8 | durable, smooth |
| X/LBG | 70:30 | 0.5 | 31.2 ± 5.2 | soft, robust |
| X/LBG | 70:30 | 0.3 | 27.7 ± 2.6 | very soft |
| X/LBG | 70:30 | 0.2 | 31.6 ± 3.1 | soft, delicate |
| X/LBG | 60:40 | 0.5 | 32.2 ± 4.8 | durable, smooth |
| X/LBG | 50:50 | 1.0 | 27.5 ± 4.4 | durable, smooth |
| X/LBG | 50:50 | 0.7 | 28.0 ± 7.7 | durable, smooth |
| X/LBG | 50:50 | 0.5 | 40.7 ± 3.4 | rough |
| X/LBG | 50:50 | 0.3 | 32.8 ± 4.5 | very soft |
| X/LBG | 50:50 | 0.2 | 35.1 ± 4.7 | soft, durable |
| X/LBG | 30:70 | 0.7 | 28.0 ± 6.2 | durable |
| X/LBG | 30:70 | 0.5 | 43.3 ± 3.1 | rough |
| X/LBG | 30;70 | 0.3 | 51.1 ± 6.0 | rough |
| X/LBG | 30:70 | 0.2 | 41.6 ± 3.9 | flimsy |
| X/G | 70:30 | 0.7 | 21.0 ± 3.2 | durable, smooth |
| X/G | 70:30 | 0.5 | 32.1 ± 3.8 | tough |
| X/G | 70:30 | 0.3 | 32.5 ± 1.8 | tough |
| X/G | 70:30 | 0.2 | 29.8 ± 3.0 | flimsy |
| X/G | 50:50 | 0.7 | 17.6 ± 3.2 | durable, smooth |
| X/G | 50:50 | 0.5 | 21.6 ± 3.9 | tough |
| X/G | 50:50 | 0.3 | 28.0 ± 5.6 | tough |
| X/G | 50:50 | 0.2 | 30.5 ± 3.7 | flimsy |
| X/G | 40:60 | 0.5 | 42.3 ± 10.1 | durable, smooth |
| X/G | 30.70 | 0.7 | 23.0 ± 4.6 | durable, smooth |
| X/G | 30:70 | 0.5 | 31.4 ± 4.9 | rough |
| X/G | 30:70 | 0.3 | 36.0 ± 3.8 | tough |
| X/G | 30:70 | 0.2 | 33.2 ± 7.2 | flimsy |
| X/LBG/G | 1:1:1 | 0.2 | 40.2 ± 2.3 | flimsy |
| X/LBG/G | 1:1:1 | 0.5 | 53.1 ± 7.1 | durable, smooth |
| X/LBG/G | 2:1:1 | 0.5 | 47.6 ± 5.6 | durable, smooth |
| X/LBG/G | 9:6:5 | 0.5 | 37.7 ± 2.6 | durable, smooth |

X = Xanthan  G = Guar gum  LBG = Locust bean gum

TABLE 2

| SAMPLE, | OBSERVATIONS |
|---|---|
| xanthan sponge | disintegrated after 17 hours |
| guar sponge | disintegrated after 17 hours |
| locust bean gum sponge | disintegrated after 43 hours |
| X/LBG 1:1 | partially disintegrated after 89 hours, fully after 163 hours |
| X/guar 60/40 | partially disintegrated after 89 hours, fully after 163 hours |
| X/guar 40/60 | partially disintegrated after 89 hours, fully after 163 hours. |
| Kalostat ® rope | partially disintegrated after 89 hours, still only partially after 163 hours. |
| Algosteril ® | partially disintegrated after 89 hours, still only partially after 163 hours. |
| Sorbsan ® pad | disintegrated into fibres immediately. |

What is claimed is:

1. A solid bioabsorbable material for use as a wound dressing, said material comprising at least 50% by weight of a mixture of xanthan and at least one galactomannan such that the weight ratio of xanthan to total galactomannan is in the range of 1:99 to 99:1 wherein the material is in the form of sponge and said sponge material is made from a solution comprising less than 1 weight percent solids of the mixture of xanthan and a galactomannan.

2. A material according to claim 1, wherein the weight ratio of xanthan to total galactomannans is in the range 10:90 to 90:10.

3. A material according to claim 2, wherein the weight ratio of xanthan to total galactomannans is in the range 25:75 to 75:25.

4. A material according to claim 1, wherein the galactomannans are selected from the group consisting of guar gums, locust bean gums and mixtures thereof.

5. A material according to claim 1, wherein at least 75% by weight of the material consists of said mixture of xanthan and galactomannans.

6. A material according to claim 1, further comprising up to 10% by weight of one or more therapeutic agents.

7. A method of making a solid bioabsorbable material for use as a wound dressing, the method comprising:

dispersing at least 50% by weight of a mixture comprising xanthan and at least one galactomannan such that the weight ratio of xanthan to total galactomannan is in the range of 1:99 to 99:1 in a solvent to form a mixed dispersion wherein the mixture comprises a solution of less than 1 weight percent solids of xanthan and galactomannan in said dispersion, and freeze-drying the dispersion to reduce said material in the form of a sponge.

8. A method according to claim 7, wherein the solvent consists essentially of water.

9. A method according to claim 8, wherein the total weight concentration of said xanthan and galactomannans in the dispersion is in the range of 2–20 mg/ml.

10. A method according to claim 7, further comprising the step of dispersing a therapeutic agent in said solvent.

* * * * *